(12) United States Patent
Mengel et al.

(10) Patent No.: US 6,167,767 B1
(45) Date of Patent: Jan. 2, 2001

(54) AUTOMATED SEQUENTIAL GAS SAMPLING SYSTEM

(75) Inventors: R. William Mengel, Great Falls, VA (US); Thomas G. Albro; John C. Berends, Jr., both of Bel Air, MD (US); Robert S. Marshall, New Market, MD (US); Christopher D. Sloop, Mt. Airy, MD (US)

(73) Assignee: RAI Corporation, Abingdon, MD (US)

( * ) Notice: Under 35 U.S.C. 154(b), the term of this patent shall be extended for 0 days.

(21) Appl. No.: 09/179,066

(22) Filed: Oct. 26, 1998

(51) Int. Cl.[7] ........................................ G01N 1/22
(52) U.S. Cl. .................. 73/863.21; 73/863.01; 73/863.23; 73/863.31
(58) Field of Search ............... 73/863.01, 863.02, 73/863.03, 862.21, 863.23, 863.24, 863.25, 863.31, 863.32, 863.33, 864.81, 864.83–864.87

(56) References Cited

U.S. PATENT DOCUMENTS

| | | | |
|---|---|---|---|
| 2,699,679 | * 1/1955 | Munger | 73/863.21 |
| 3,540,261 | 11/1970 | Scoggins | 73/28 |
| 3,841,160 | * 10/1974 | Iwao | 73/864.87 |
| 3,849,070 | * 11/1974 | Gurza et al. | 73/864.74 X |
| 3,884,081 | 5/1975 | Griffith | 73/421.5 R |
| 4,014,216 | * 3/1977 | Thornton et al. | 73/863.23 |
| 4,035,168 | * 7/1977 | Jennings | 73/864.85 |
| 4,274,285 | * 6/1981 | Purgold | 73/863.31 |
| 4,351,802 | * 9/1982 | Beylis et al. | 73/864.83 |
| 4,414,857 | * 11/1983 | Brazhrikov et al. | 73/864.87 X |
| 4,517,851 | 5/1985 | Tice | 73/864.91 |
| 4,584,887 | 4/1986 | Galan | 73/864.35 |
| 4,815,325 | * 3/1989 | Avesette | 73/864.86 X |
| 4,823,623 | * 4/1989 | Carpenter et al. | 73/864.74 |
| 4,869,117 | 9/1989 | McAndless et al. | 73/864.34 |
| 4,890,502 | 1/1990 | Elias et al. | 73/864.85 |
| 4,976,924 | 12/1990 | McAndless et al. | 422/99 |
| 5,326,532 | * 7/1994 | Taylor | 73/863.33 X |
| 5,433,122 | * 7/1995 | Boyd et al. | 73/864.86 |
| 5,553,508 | 9/1996 | Dabbert et al. | 73/63.02 |

OTHER PUBLICATIONS

J. of Chromatography, 395 (1987)531–538; A. H. Lawrence, "Sample Interface, for Transferring High–Boiling Compounds from Sample Adsorption Tubes Onto Capillary Gas Chromatographic Columns" month not given.

\* cited by examiner

Primary Examiner—Thomas P. Noland
(74) Attorney, Agent, or Firm—Roland H. Shubert

(57) ABSTRACT

A gas sampling system includes a sample trapping module having a gas pump and a power supply, and a removable magazine that fits within a port of the trapping module. The magazine contains a non-volatile electronic memory, which controls operation of the trapping module, and has a rotating carousel for holding sample tubes. Individual sample tubes are sealed at each end by a cap that has a needle-pierceable septum, and contain a solid collector material to trap chemical and biological contaminants in a gas sample drawn through the sample tube. Individual sample tubes are moved into and out of a sampling location by incremental rotation of the carousel and, while at the sampling location, a pair of hollow bore needles are inserted through the sample tube end caps to allow the drawing of a gas sample through the tube.

16 Claims, 10 Drawing Sheets

AUTOMATED SEQUENTIAL GAS SAMPLING SYSTEM

FIELD OF THE INVENTION

This invention relates generally to sampling devices for determining the nature and quantity of chemical and biological contaminants in air and other gases.

More specifically, this invention concerns a gas sampling system that includes a sample trapping module, a magazine holding a plurality of collector-filled sampling tubes, a control that operates the trapping module, and an interface to analytical instruments.

DESCRIPTION OF RELATED ART

There is a large and continuing need for identifying and monitoring the level of pollutants in air and in industrial gas streams. In the past this task was usually performed by obtaining a sample of the air at the monitoring site, and transporting that sample to a laboratory for analysis. Samples were ordinarily obtained by manually filling a sampling container, such as a plastic bag, a hypodermic syringe, or an evacuated metal or glass vessel, and sealing it for transport.

That approach was very expensive, particularly in terms of the personnel needed for periodically taking samples over a long time interval. Consequently, there was developed a number of sampling devices for collecting air samples at predetermined intervals over an extended time period. One such device is shown in the Griffith patent, U.S. Pat. No. 3,884,081. The Griffith sampler uses a plurality of piston pumps that may be hypodermic syringes of appropriate capacity. The plunger of each pump is retracted by mechanical means at a scheduled time to draw an air sample into the pump barrel.

Another sampler that operates in the same general fashion is disclosed in U.S. Pat. No. 3,540,261, to Scoggins. Scoggins provides a magazine containing a number of individual sample containers. The magazine is powered by a time controlled drive system that sequentially indexes the sample containers into registry with a monitoring station where each container is connected with a vacuum source that draws a gas sample through the container, and stores the sample for further processing.

Sampling devices that take a bulk air sample for transport and later analysis are often inappropriate for use in those circumstances in which the contaminant being monitored is present in small concentration, in the parts per million or even parts per billion range. The size of the sample that is collected is often too small for the contaminant to be detected and its concentration measured. That requirement has led to the development of sampling devices which employ sample containers that preferentially extract a contaminant from the sampled gas stream, and hold the trapped contaminant for later release and analysis.

Two patents illustrate that approach to sampling. The first is a patent to Galen, U.S. Pat. No. 4,584,887, which discloses a sampling system having a sample module that may be detached from a flow assembly module. The sample module includes a plurality of small parallel tubes arranged longitudinally about the periphery of a circular frame. Each tube contains a sorbent material that functions to extract and hold contaminants from an air stream passing through the tube. Because most contaminants of interest are organic compounds, the sorbent material is chosen to adsorb those compounds while allowing inorganic compounds to pass through the tube substantially unimpeded. In use, the sample module is mated with the flow assembly module, and sample tubes are sequentially indexed to and connected in series with the sampler inlet and exhaust ports of the flow assembly module by means of a selector valve. A predetermined volume of air is then pumped through the indexed sample tube, and the airborne contaminants are trapped on the sorbent material.

The second patent of interest here is U.S. Pat. No. 4,869,117 that issued to McAndless et al. Like Galen, the McAndless patent uses a cylindrical sample magazine which holds a plurality of small sample tubes that are packed with a solid adsorbent. The sample tubes are symmetrically arranged in a circle about the longitudinal axis of the magazine. The McAndless device differs from that of Galen in that the individual sample tubes are not isolated from each other by way of valve means. Instead, McAndless et al provide a sampling inlet and outlet extending through the magazine housing at a sampling position. Individual tubes are sequentially advanced to and then from the sampling position. While at the sampling position, both ends of the sample tube are sealed so that the tube is positioned in series between the sample source and an air pump which draws an air sample through the tube.

Finally, Lawrence in a paper published in the *Journal of Chromatography*, 395 (1987) 531–538, Elsevier Science Publishers, describes an interface for transferring high boiling compounds from a sample adsorption tube to the column of a gas chromatograph for analysis. The sample tubes described and illustrated by Lawrence are generally similar to those used by McAndless et al.

Despite the developments in sampling techniques described in the prior art, there still exists a need for systems that can obtain a large number of samples at remote and unattended locations, and maintain the integrity of each sample taken until analysis is complete. The system of this invention fills that need.

SUMMARY OF THE INVENTION

The sampling system of this invention includes a sample trapping module, a magazine, sample tubes, and an interface means that functions to enable cooperation between the magazine, the sample tubes and an analytical instrument. The sample trapping module is arranged to hold the magazine during sampling, to sequentially index sample tubes into and out of sampling position within the magazine, to monitor sampling conditions and to collate that data with each individual sample, and to accept control instructions from non-volatile memory carried in the magazine. In turn, the magazine houses a plurality of individual sampling tubes and contains memory means adapted to control operation of the trapping module and to accept and preserve data relating to the samples that are taken by the sample trapping module. Sample tubes used in the invention consist of elongated, sealed tubes which contain a solid collector material that can selectively remove a chemical or biological contaminant of interest from a gas stream that is passed through the tube. Lastly, the interface means is arranged to facilitate the removal of sample tubes from the magazine, and to release contaminants from the collector material contained within the sampling tubes for analysis using conventional procedures.

Hence, it is an object of this invention to provide an unattended, integrated sampling system for repeatedly sampling a gas or air stream at predetermined times to concentrate and collect chemical and biological contaminants for later analysis.

It is a further object of this invention to provide a novel sampling magazine that is arranged to house a plurality of sampling tubes, and which contains non-volatile memory that controls the sampling process and stores data relating to the sample taken by each individual sampling tube.

Yet another object of this invention is to provide a novel sampling tube for use in the sampling system.

Other objects of this invention will be evident from the following detailed description of the invention.

DETAILED DESCRIPTION OF THE INVENTION

Figure 1:
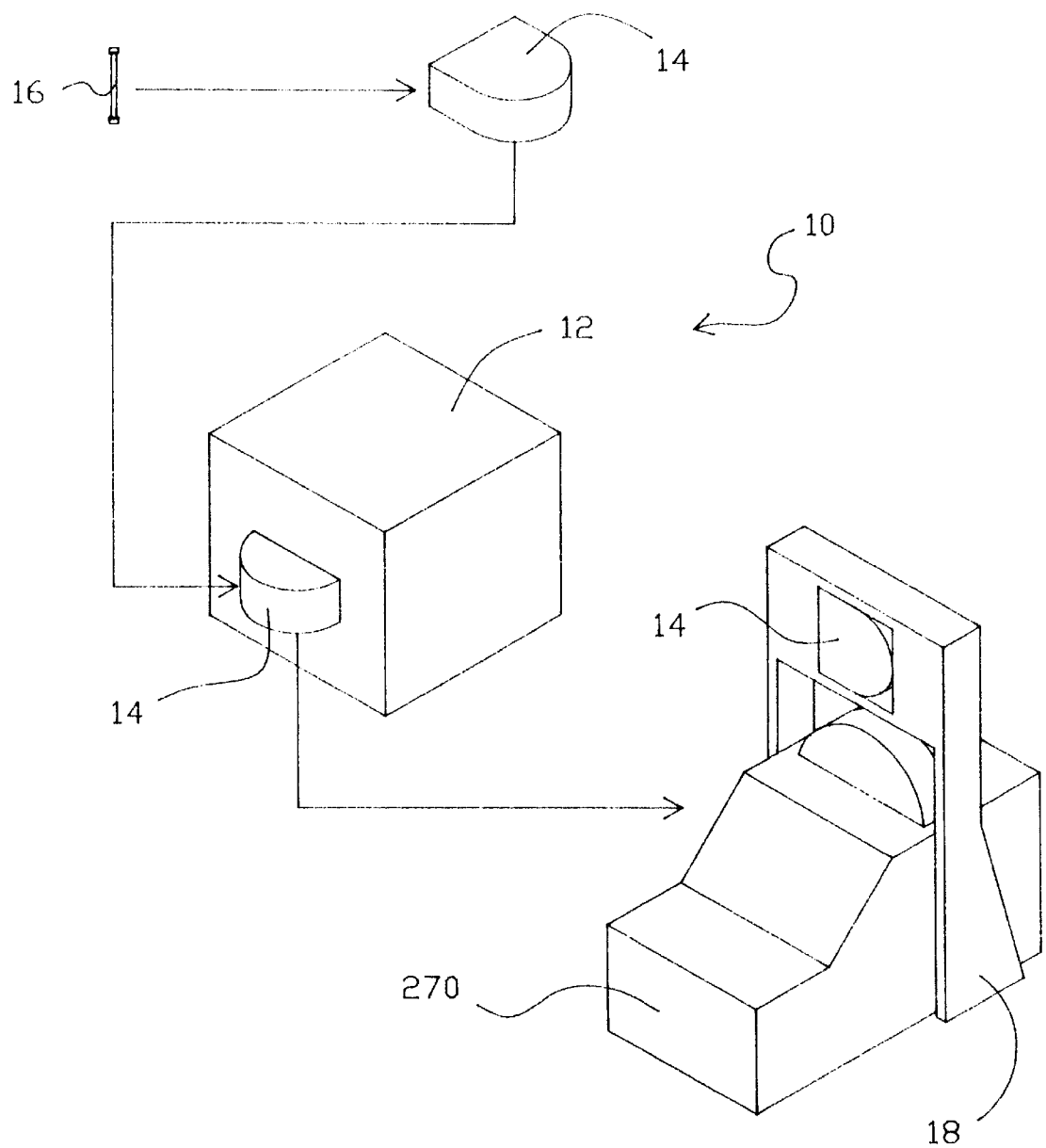
FIG. 1 is a schematic view of the major elements of the sampling system, showing how the elements interact.

FIG. 1 schematically depicts the major elements of the sampling system 10 and the relationship of those elements one to another. System 10 includes a sample trapping module 12, a magazine 14, a plurality of sample tubes 16, and an interface means 18. The first three major elements, the trapping module, magazine, and sample tubes, constitute the field portion of the system while interface means 18 in cooperation with desorber 270 is used at an analytical laboratory to operably interconnect the magazine to an analytical instrument.

In operation, magazine 14 is first loaded with sample tubes 16 and the filled magazine is inserted into port 20 of the trapping module 12 to ready the field portion of the system for sampling. The system field portion is taken to a sampling location, and samples of the atmosphere at the sampling location are obtained by drawing a predetermined volume of gas through individual sample tubes.

The sample tube design is a critical feature of the sampling system of this invention as it facilitates the automation of the entire sample collection and analysis process. While samplers which use so-called "minitubes" are finding increasing acceptance, there has not yet developed an industry standard for physical dimensions and mechanical configuration of such tubes. Nevertheless, it is preferred that the sample tubes used in the sampling system of this invention conform to the physical dimensions of those sample tubes that are compatible with the automatic thermal desorption unit which is manufactured by Perkin Elmer Corporation as that system controls a large share of the relevant commercial market. Those particular sample tubes comprise an elongated tube having a removable cap at each end. The tubes are manufactured of stainless steel, glass, or glass lined stainless steel having an outside diameter of 0.250", a bore of 0.190", and a length of 3.50".

Figure 2:
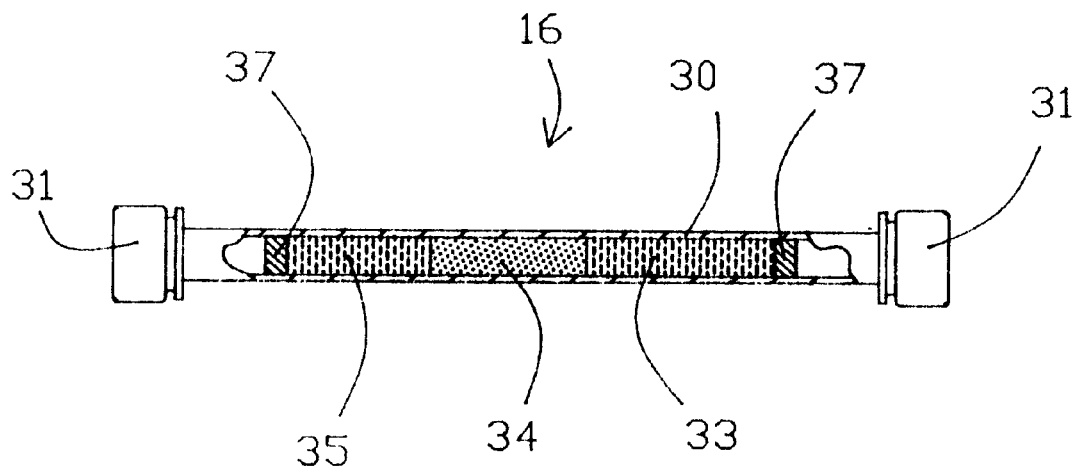
FIG. 2 is a partial sectional view of a sample tube that is used with the sampling system of this invention.
Figure 3:
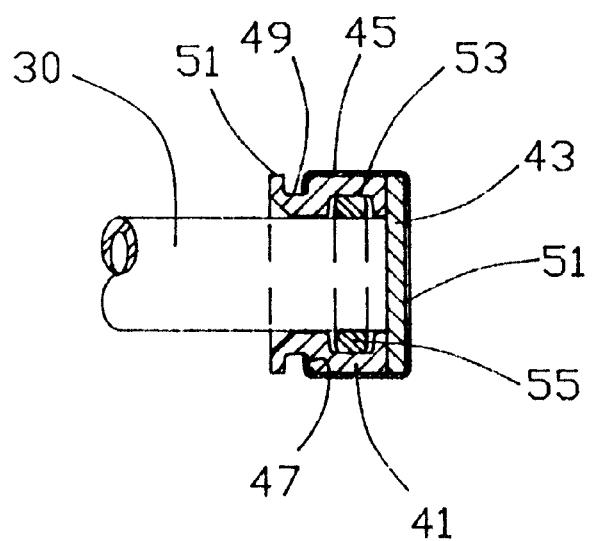
FIG. 3 is a cross-sectional view of a sample tube end closure.

Referring now to FIGS. 2 and 3, there is illustrated a preferred structure of the sample tubes that are used in the inventive system. Referring first to FIG. 2, sample tube 16 is shown in partial cross section and includes a tube body 30 and a pair of end caps 31. The end caps are preferably manufactured from a chemically inert material which suitably may be a polytetrafluoroethylene polymer such as Teflon®, and use an O-ring to form a seal between the cap bore and the outer surface of the sample tube. Tube body 30 and end caps 31 preferably conform in physical dimensions to those sorbent tubes and caps used in the Perkin Elmer automatic thermal desorber system. The central portion of the tube bore is filled with a collector material 33, 34, 35 that is selected to remove specific contaminants from the gas stream being sampled. The collector material is held in place within the tube bore by means of porous plugs 37 of glass wool or similar material. It must be arranged to allow reasonably free flow of gas through the tube during the sampling process while at the same time ensuring thorough and extended contact between the gas and the collector material. The collector material is ordinarily employed in particulate form, and a size range of 20/60 mesh is usually appropriate.

Composition of the collector material is tailored to the specific suite of contaminants that is being monitored. In many instances, the composition of collector materials 33, 34 and 35 are different one from another, especially in those circumstances wherein the presence and concentration of a variety of different contaminants is being monitored. In other instances, the composition of collector materials 33, 34 and 35 may be the same, especially if only one, or one type of contaminant, is to be monitored. For example, if a user is monitoring ambient air for chemical contaminants having a range of activities or molecular weights, then the use of several different adsorbents as collector materials in the same sample tube results in obtaining more complete and representative samples. On the other hand if a specific contaminant is being monitored, then use of a collector material that is tailored to adsorbing and trapping that particular contaminant offers advantages. In some circumstances, particularly when the composition of collector materials 33, 34 and 35 differs, it is important to fix the direction of gas flow through the sample tube. In order to obtain that result, there is provided orienting indicia that may be one or more orienting grooves 39 about the exterior of tube body 30, adjacent one end thereof so that individual sample tubes can be placed in the same orientation within magazine 14. Those same orienting indicia are used to ensure as well that the sample tubes are correctly oriented during desorption of contaminants from the collector material for analysis.

In addition to chemical contaminants, the system of this invention is useful in monitoring air and other gas samples for the presence of biological contaminants such as, for example, disease carrying organisms, spores and viruses. For this use, the collector material 33, 34 and 35 may comprise either a trapping substance such as a high efficiency filter, or a biological culture medium that include nutrient systems for the artificial cultivation of the cells or organisms of interest. An air or gas sample is drawn through the media containing sample tube wherein biological contaminants carried in the air stream contact and are caught by the trapping substance or inoculate the culture media. The sample tube is then transported to a laboratory for analysis using conventional techniques, including DNA analysis, to identify the contaminant.

Turning now to FIG. 3, there is shown a preferred embodiment of the sample tube end caps 31. While simple in appearance, the end caps serve a number of critical functions in the sampling system of this invention. The end caps must provide a seal for the sample tubes that will prevent contamination of the collector material prior to sampling, but also must be easily removed and replaced by automated sample analyzing equipment including, for example, automatic thermal desorbers. During sample taking, the end caps must seal tightly enough to prevent leakage to the vacuum that is drawn within the sample tube. After a sample has been obtained, the end caps must seal tightly enough to maintain the sample in isolation, often for extended periods of time, until an analysis is performed. The end caps also must allow entry of a hollow bore needle during the sampling procedure. Lastly, the caps must be constructed of extremely inert materials so that there is essentially no chance of interaction between sample constituents and the cap material. For that reason, it is preferred that all parts of the end cap that come into contact with the sample be made of or coated with an inert fluorocarbon polymer such as Teflon® or similar polymers.

Each end cap 31 includes a generally cylindrical cap body 41 having an internal diameter sized to make a sliding fit over the outside surface of tube body 30. A septum 43 closes one end of cap body 41, and is secured in place by means of crimp cap 45 that is anchored to body 41 about shoulder 47. Shoulder 47, in turn, is formed by a notch 49 that is cut into cap body 41 adjacent its open end leaving a flange 51 at the open end of the cap body. A circular groove 53 is cut into the inner surface of cap body 41 to hold and seat O-ring 55 which seals the sample tube when the end cap is in place. The depth of groove 53 determines the pressure that is developed between the O-ring and the tube surface, and so determines the strength and integrity of the seal formed between the end cap and the sample tube. That seal must be sufficiently strong to prevent leakage when a partial vacuum is drawn in the tube during sampling, but it must not be so strong as to interfere with operation of analytical equipment that removes and replaces the end caps on the sample tubes. A groove depth that produces a seal tightness which requires about 2 to 3 pounds of force to pull the end cap from the tube end is about optimum.

An opening is provided in the center of the crimp cap 45 that exposes the outside central portion 57 of septum 43. Crimp caps suitable for use here are commercially available, and are routinely used on autosampler vials in gas and liquid chromatography applications. During the sampling procedure a hollow bore needle is inserted through the exposed septum area 57 at each tube end. A stream of the gas being sampled enters through one of the needles, contacts the collector material 33, 34, 35, and exits through the other needle.

Figure 4:
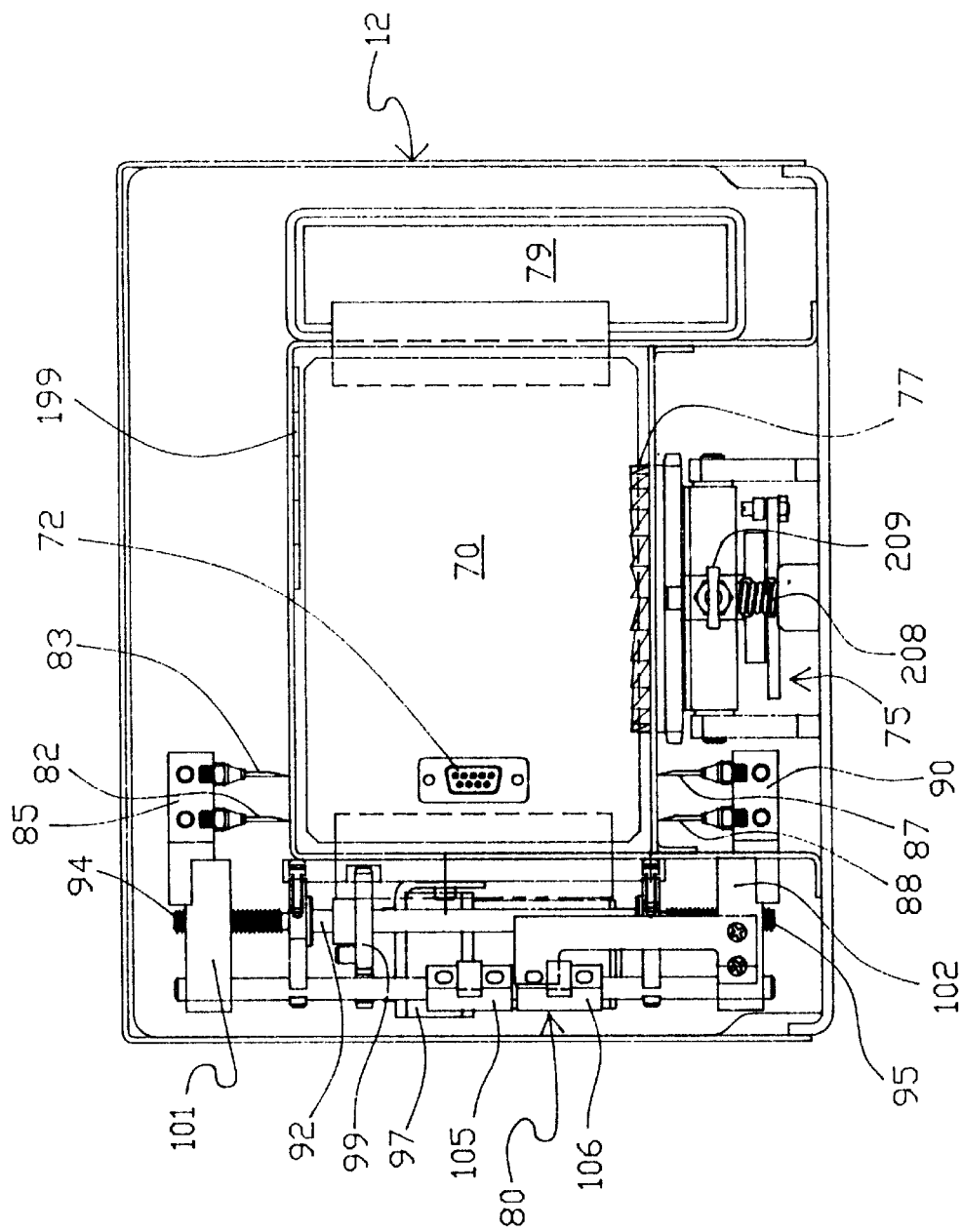
FIG. 4 is a front view of the sample trapping module showing its operating parts.
Figure 5:
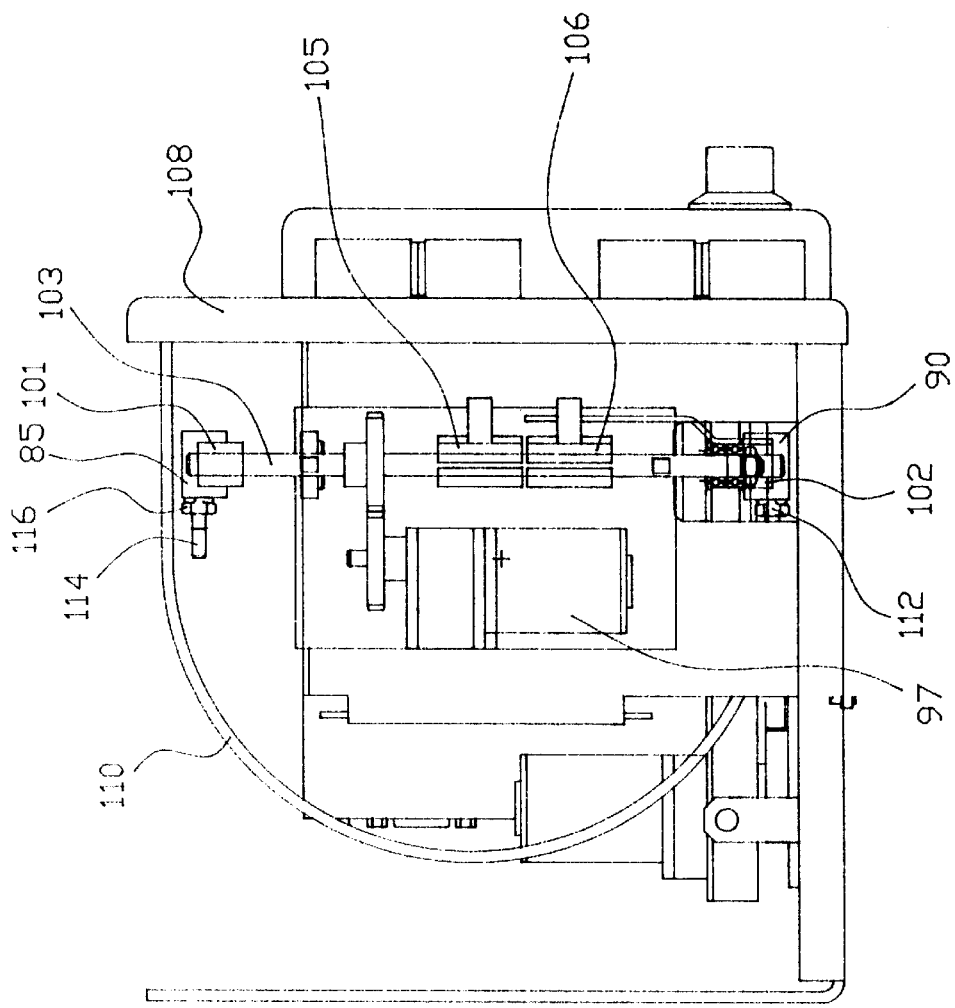
FIG. 5 is a an end view of the needle drive mechanism of the sample trapping module of FIG. 4.
Figure 9:
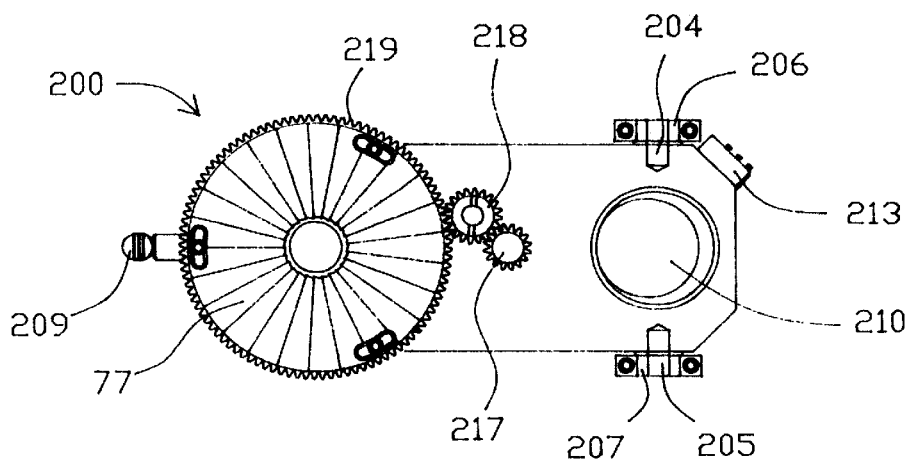
FIG. 9 is a top view of the magazine carousel drive mechanism of the sample trapping module.
Figure 10:
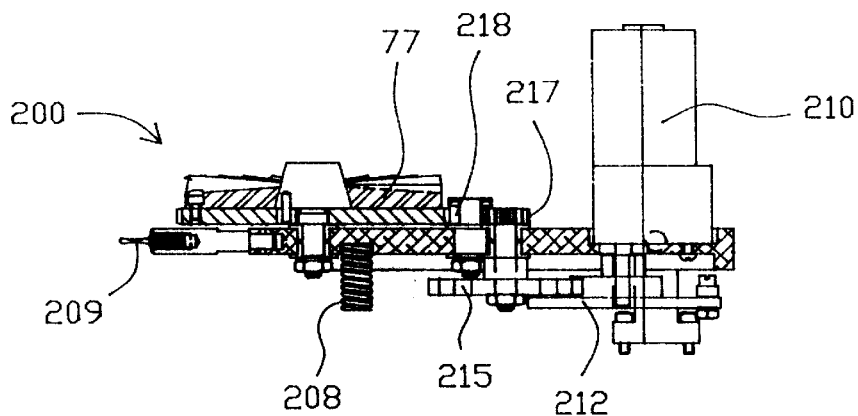
FIG. 10 is a side view of the drive mechanism of FIG. 8.
Figure 11:
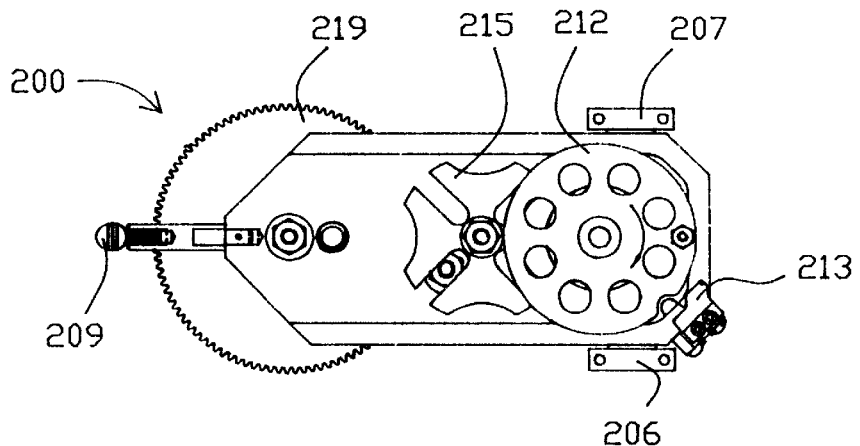
FIG. 11 is a bottom view of the drive mechanism of FIG. 8.

Turning now to FIGS. 4 and 5, there is shown details of sample trapping module 12. FIG. 4 shows the trapping module 12 with the front housing panel removed. Module 12 includes a port 70 into which magazine 14 fits. A plug 72 is provided at the rear of port 70 to provide electrical connection to memory means that are contained within magazine 14 when the magazine is seated in the port. A magazine drive assembly, which is shown generally at 75 and is detailed in FIGS. 9, 10 and 11, is located at the bottom of the module below port 70. Drive assembly 75 serves to rotate sample tubes carried within magazine 14 to and from a sampling position by incremental rotation of clutch drive plate 77. Overall control of the trapping module 12 resides in operations module 79 which includes a positive displacement pump to draw sample, and controller means that commands the operational sequence of the system through instructions residing in the memory means 130 (FIG. 6) within magazine 14.

A needle drive assembly, shown generally at 80, is arranged to insert hollow bore needles through the exposed septum area 57 at each end of a sample tube 16 at the time that tube is indexed at the sampling position of magazine 14. In a first embodiment, the needle drive assembly inserts two needles, one at each end, into a capped sample tube. In a second and preferred embodiment, a pair of upper needles 82,83 are mounted upon upper traveling needle block 85, and a pair of lower needles 87,88 are mounted upon lower traveling needle block 90. In this preferred embodiment, sequential pairs of sample tubes 16 are arranged adjacent one another at the sampling position in alignment with the upper and lower needle pairs.

The upper and lower needle blocks are driven toward and away from each other by means of a rotating shaft 92 that has opposite lead threads on its upper and lower ends, 94 and 95 respectively. Shaft 92 is powered by a motor and reduction gear box 97 through a gear train 99. The two oppositely threaded ends of shaft 92 engage upper and lower slide blocks 101 and 102 which are mounted on guide bar 103 and carry the upper and lower needle blocks 85 and 90. The travel of each of the needle blocks is sufficient to allow clean penetration of the needle tip through the sample tube septum, and in practical terms, is on the order of 1 to 1.5 cm. Total travel of the needle blocks Ls limited by switch means controlled by two photo sensors 105 and 106 that are mounted on guide bar 103. A flag mounted on either the upper or lower slide block interrupts the photo sensors to produce a signal that stops the motor 97.

FIG. 5 shows an end view of the needle drive assembly 80. Considering FIG. 5 in association with FIG. 4, the arrangement of motor and gear box 97, gear train 99, and guide bar 103 can be more clearly discerned. A stream of gas to be sampled is supplied by way of manifold 108. A representative sample stream is pulled from manifold 108 by way of flexible inlet conduit 110 that is connected to fitting 112 on lower needle block 90. A passage within needle block 90 allows closed communication between conduit 110 and needles 87 and 88. Conduit 110 is formed as an arcuate loop of large diameter relative to the diameter of the conduit so as to minimize bending stresses as needle block 90 moves up and down during the sampling procedure. In similar fashion, a sample exhaust conduit 112 connects to upper needle block 85 through fitting 114 providing a closed path between upper needles 82 and 83 and conduit 112. The other end of conduit 112 connects to the suction side of a positive displacement pump, as is shown diagrammatically in FIG. 12.

Figure 6:
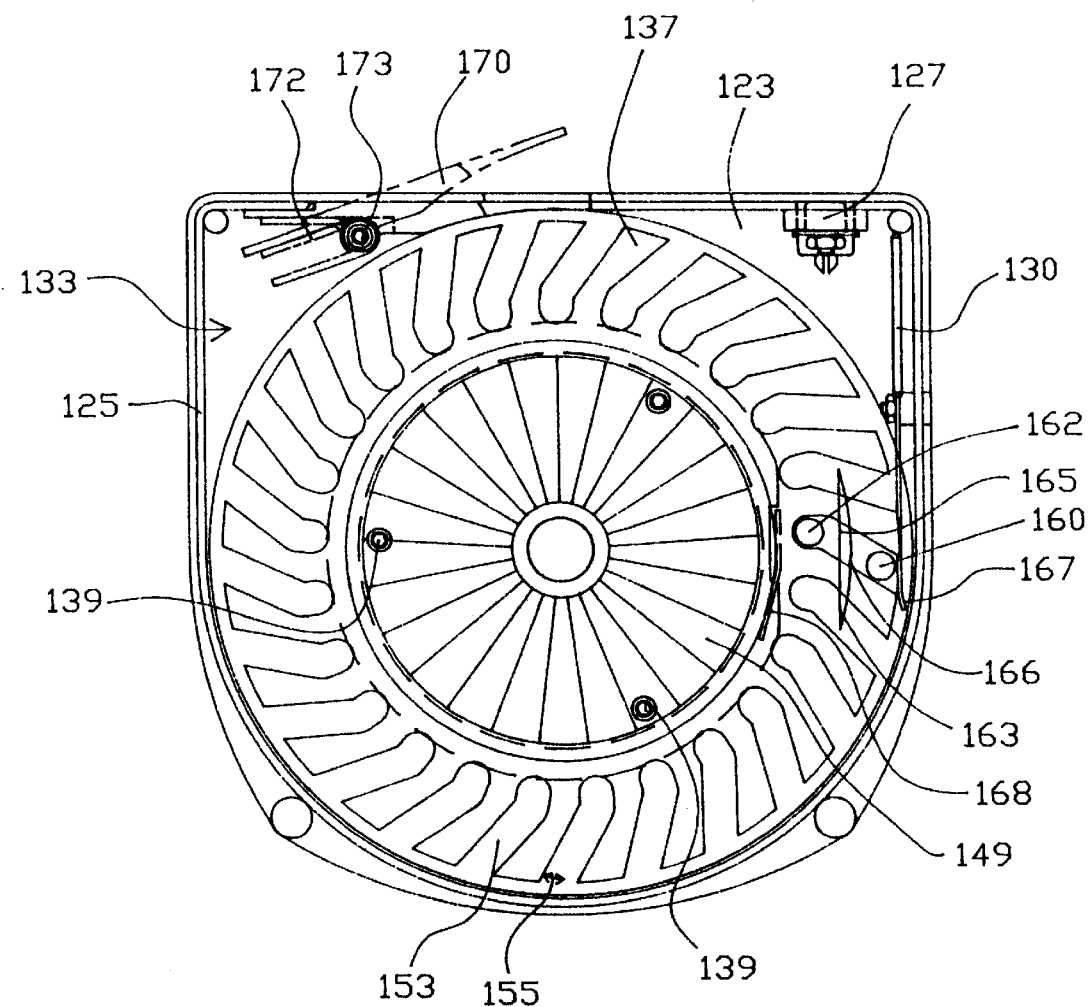
FIG. 6 is a bottom, internal view of the sampler magazine.
Figure 7:
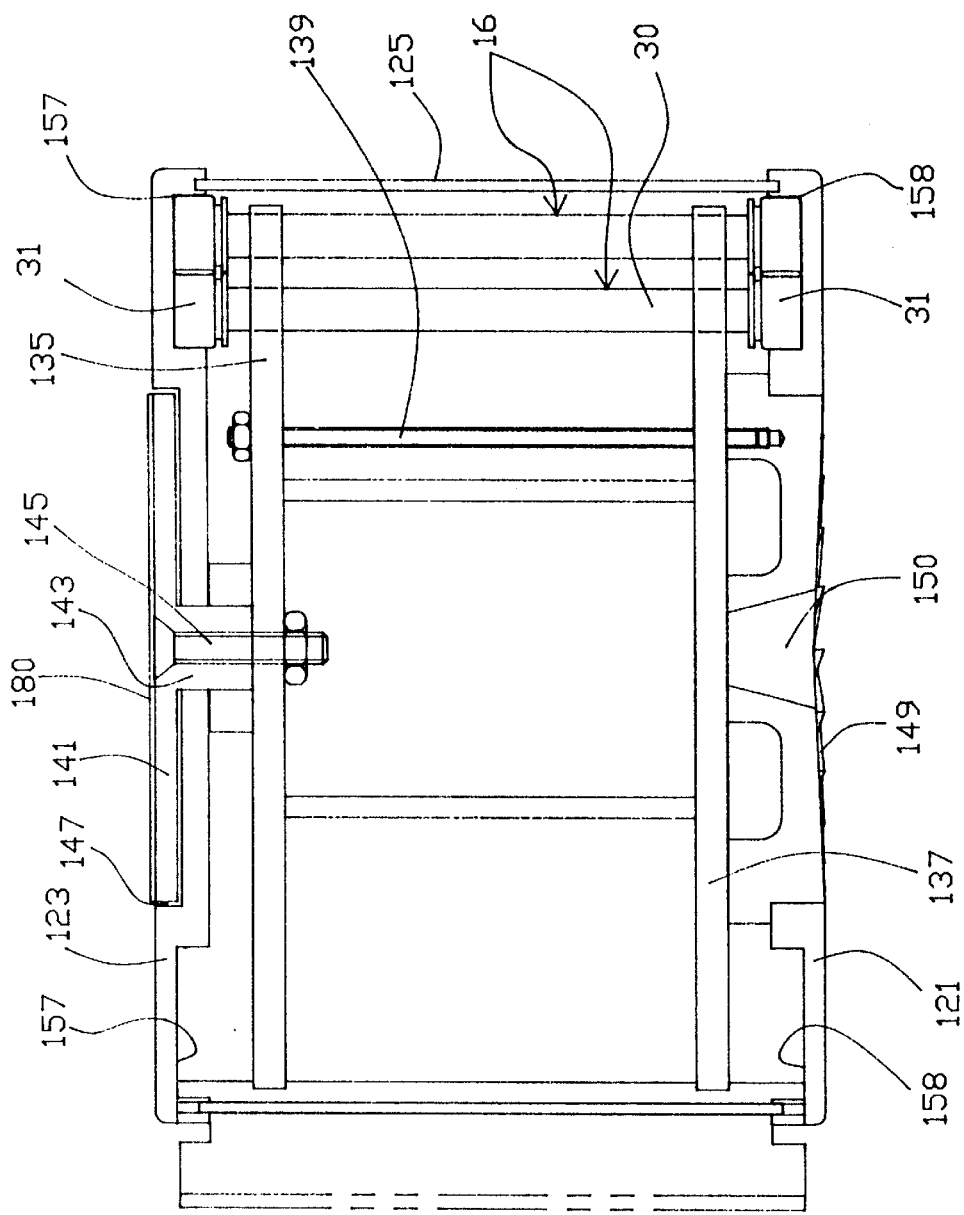
FIG. 7 is a front view of the sampler magazine showing its internal construction.

Structural details of magazine 14 are shown in FIGS. 6 and 7. Referring now to those Figures, FIG. 6 is a bottom view of magazine 14 with the bottom closure plate removed, while FIG. 7 is an outline side view showing the arrangement of sample tubes within the magazine. Magazine 14 includes a closed housing that comprises a bottom plate 121, a top plate 123, and a side plate 125 extending around the periphery of the housing between the top and bottom plates. A connector plug 127 is located on the rear side plate and is arranged to make mating electrical connection with plug 72 when magazine 14 is inserted into port 70. An electronic memory comprising a printed circuit board containing non-volatile memory chips 130 is located within the magazine. Memory 130 is arranged to accept and store data from operations module 79 that relate to individual samples arid, in a preferred embodiment, to use data that is impressed within that memory to direct operations module 79 in the taking of samples by the system as will be described in more detail later.

Rack means are provided within the housing to position and hold a plurality of sample tubes. Those rack means preferably are arranged as a rotating magazine carousel that is indicated generally at 133. Carousel 133 is arranged centrally within the housing of magazine 14, and includes a circular upper sample tube holder plate 135 and a lower circular tube sample holder plate 137. The upper and lower tube holder plates are held in a parallel, spaced apart relationship by a plurality of posts 139. A rotating block having a circular top flange 141 and a central bottom post 143 is connected to carousel upper tube holder 135 by bolt means 145. Flange 141 slidingly fits within circular recess 147 formed on the outer side of top plate 123, and is free to rotate within that recess. A driven clutch plate 149 is secured to the bottom of lower tube holder 137 by means of standoff post 150, and is arranged to engage clutch drive plate 77. The carousel is caused to incrementally rotate about the axis formed by bolt means 145 by a corresponding rotational movement of clutch drive plate 77.

A plurality of sample tube accepting slots 153, a total of twenty-five in the embodiment illustrated, extend inwardly from the circumference and toward the center of upper and lower tube holders 135 and 137 as is best seen in FIG. 6. Each slot in the upper tube holder 135 is oriented to be directly above a corresponding slot in the lower tube holder so that sample tubes held within the slots are aligned vertically, parallel to each other and to the rotational axis of carousel 133. The width of slots 153 is set to be slightly larger than is the diameter of tube body 30 so that sample tubes freely slide back and forth along the slot. Each of slots 153 may be sized to hold a single sample tube, or in the preferred embodiment illustrated in the drawings, are sized to accommodate two sample tubes per slot. Thus, carousel 133 in the illustrated embodiment has the capacity for holding fifty sample tubes. Slots 153 may be oriented along radial lines, and that arrangement is preferred when the slots are sized to hold a single tube. When the slots 153 are sized to hold two tubes, it is preferred that the slots be oriented at an acute angle 155 to a radius of the top plate so that the inner tube in each slot nests between two adjacent outer tubes. That arrangement allows the carousel diameter, and hence the magazine size, to be reduced. Angle 155 may appropriately range between 15° and 45°.

As is best seen in FIG. 7, a circular guide groove 157 is provided in the bottom side of magazine top plate 123. A corresponding groove 158 is provided in the top side of magazine bottom plate 121. Grooves 157 and 158 form a track in which pairs of sample tubes 16 slidably move. Width of grooves 157 and 158 is set to accommodate the end caps 31 of the sample tubes 16, while the vertical spacing between grooves 157 and 158 is slightly greater that the length of a sample tube 16. Sample tubes are loaded into and removed from magazine 14 through door 170 located on the magazine side plate, and shown by dashed outline in its open position. Door 170 pivots about door pin 173, and is biased to the closed position by a torsion spring 172 that wraps around pin 173.

Carousel 133 is caused to rotate stepwise, one twenty-fifth of a revolution per step, to bring pairs of sample tubes to and away from a sampling location. The sampling location is defined by a pair of sampling ports, 160 and 162, that extend through top plate 123 and bottom plate 121. As a pair of sample tubes is moved into the sampling location, the tubes are forced into true alignment with the sampling ports 160 and 162 by divider means 163 which has detents 164 and 165 machined therein. Outer track spring 167 and inner track spring 168 urge the end caps of individual sample tubes into the detents thus positioning the sample tubes in alignment with the sampling ports. Sampling ports 160 and 162 are positioned to be in alignment as well with upper needle pair 82,83 and lower needle pair 87,88.

A sample is taken by driving the two needle pairs toward one another by activating motor 97 until the needle points have penetrated through the septa 43 that close the sample tube ends. A predetermined volume of gas is drawn through each sample tube, and the needle pairs are then moved apart by reversing motor 97. Carousel 133 is advanced another step, and the system is then ready to take another pair of samples. That procedure continues until sampling is complete, or until all of the sample tubes carried in the magazine have been used.

Individual samples are identified by a number that is assigned according the position of the sample tube within the magazine. Sample tube position, in turn, is defined by the rotational position of carousel 133 relative to sampling ports 160 and 162, and further by the slot position of the sample tube; whether it is the inner or the outer tube within the tube slot 153. In a preferred embodiment, the rotational position of carousel 133 is determined by a signal generating means that produces a different binary signature for each incremental rotational position of the carousel. That signal generating means preferably comprises a patterned mask, or encoder plate, 180 of light and dark sectors. Encoder plate 180 forms the outer surface of top flange 141, and is patterned as a series of sectors 181, 182, 183, 184, and 185 that are radially arranged in concentric rings. Each sector includes an arc 187 that subtends an angle proportional to the incremental rotation of the carousel from one sampling location to the next. In the magazine embodiment illustrated, which provides for twenty-five sample tube slots, arc 187 would subtend an angle of 14.4°.

Figure 8:
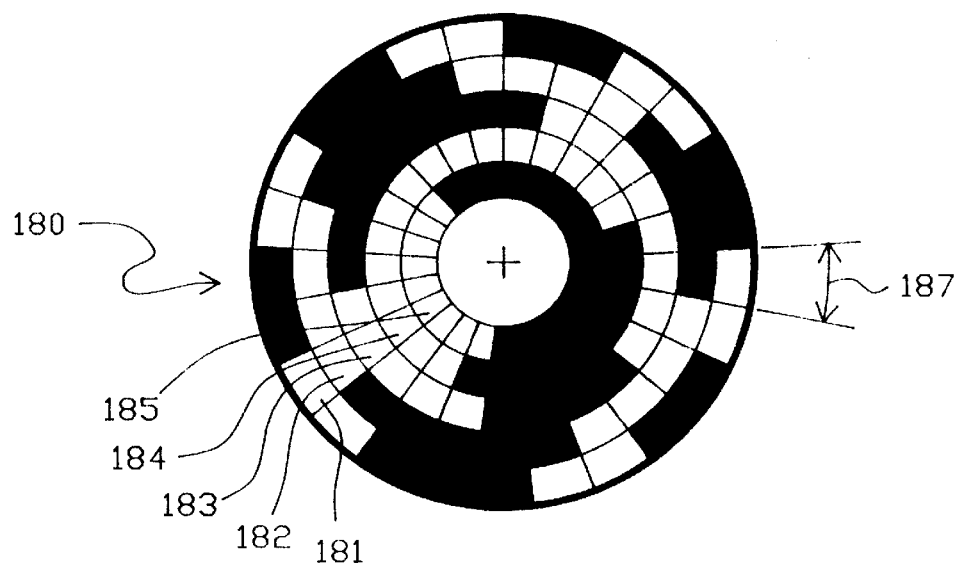
FIG. 8 is a view of the sampler magazine encoder plate that signals the rotational position of the magazine.

The entire area of each sector is either light or dark. An array of detectors 190 (FIG. 4), one for each concentric ring, is located at the top of magazine port 70. Each detector is arranged to respond to radiation only when a reflective object passes its view, and the detectors may conveniently comprise an infrared emitting diode and a phototransistor. As may be appreciated from a study of FIG. 8, the sectors making up each radial group may be arranged in a pattern of light and dark to give each rotational location of the carousel a unique binary signature. For example, that radial series of sectors 181, 182, 183, 184 and 185 may be assigned the home carousel position, and a reflective sector would be positioned below each detector. All detectors would then respond to the reflected radiation, and the resulting binary signal would be 11111 (assigning a 1 to a detector responding to radiation, and a 0 to a detector that is not.) Rotation of the carousel in a counter-clockwise direction by one incremental amount would then produce a binary signal 11110, and so on. Sample identification data produced by detector array 190 is stored in memory 130 along with other data that characterizes each particular sample.

FIGS. 9, 10 and 11 present differing views of the magazine carousel drive assembly, shown generally at 200, with FIG. 9 being a top view thereof, FIG. 10 a side view, and FIG. 11 a bottom view. Carousel drive assembly 200 functions to rotate carousel 133 in equal increments about its axis to present successive pairs of sample tubes 16 into alignment with sample ports 160 and 162. Referring now to FIGS. 9, 10 and 11 in combination, assembly 200 includes a drive train support plate 202 which is pivoted at its rearward end about pivot pins 204 and 205 that are supported by mounting brackets 206 and 207 respectively. Clutch drive plate 77 is mounted at the forward end of support plate 202, and is biased upwardly into an engagement position with driven clutch plate 149 of carousel 133 by spring means 208. The application of pressure on thumb pad 209 moves plate 202 downwardly which compresses spring 208 and disengages clutch drive plate 77 from clutch driven plate 149 so that magazine 14 may be inserted into or removed from port 70.

A gear motor 210 is mounted at the top rear of support plate 202, and drives Geneva wheel 212. Motor 210 is started upon command from an executive microprocessor 255 (FIG. 13), and is stopped by action of limit switch 213 after turning Geneva wheel 212 one complete revolution. Geneva wheel 212 is coupled through star wheel 215 and a gear train to incrementally rotate clutch drive plate 77. The gear train includes a driver gear 217 that is direct coupled to star wheel 212, idler gear 218, and driven gear 219. Gears 217 and 219 are proportioned such as to provide the desired incremental angular rotation of clutch drive plate 77. In the embodiment illustrated, clutch drive plate 77 rotates exactly ½₅th of a revolution for each full revolution of Geneva wheel 212.

Figure 12:
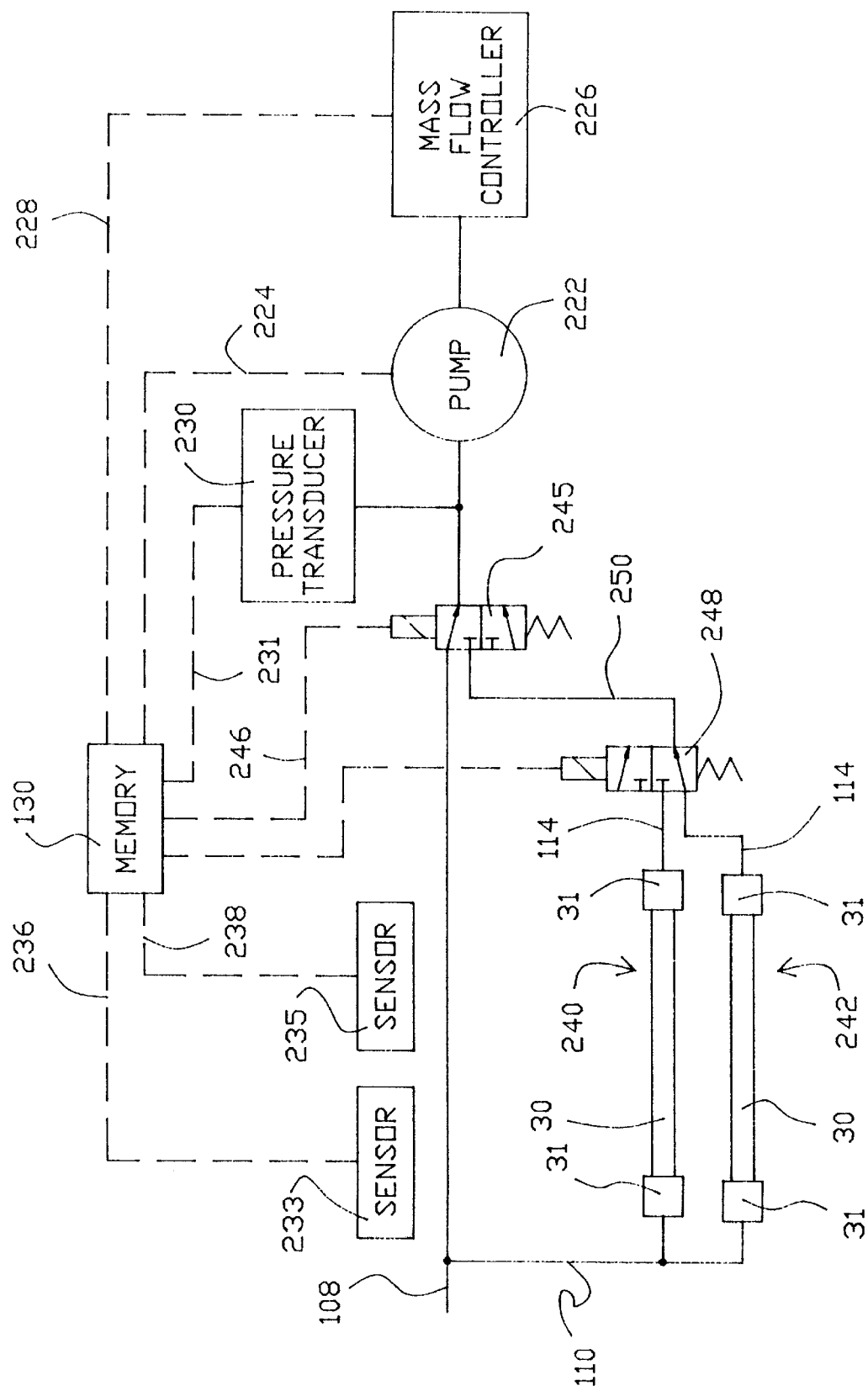
FIG. 12 is a schematic depicting the operational control of the sampling process.
Figure 13:
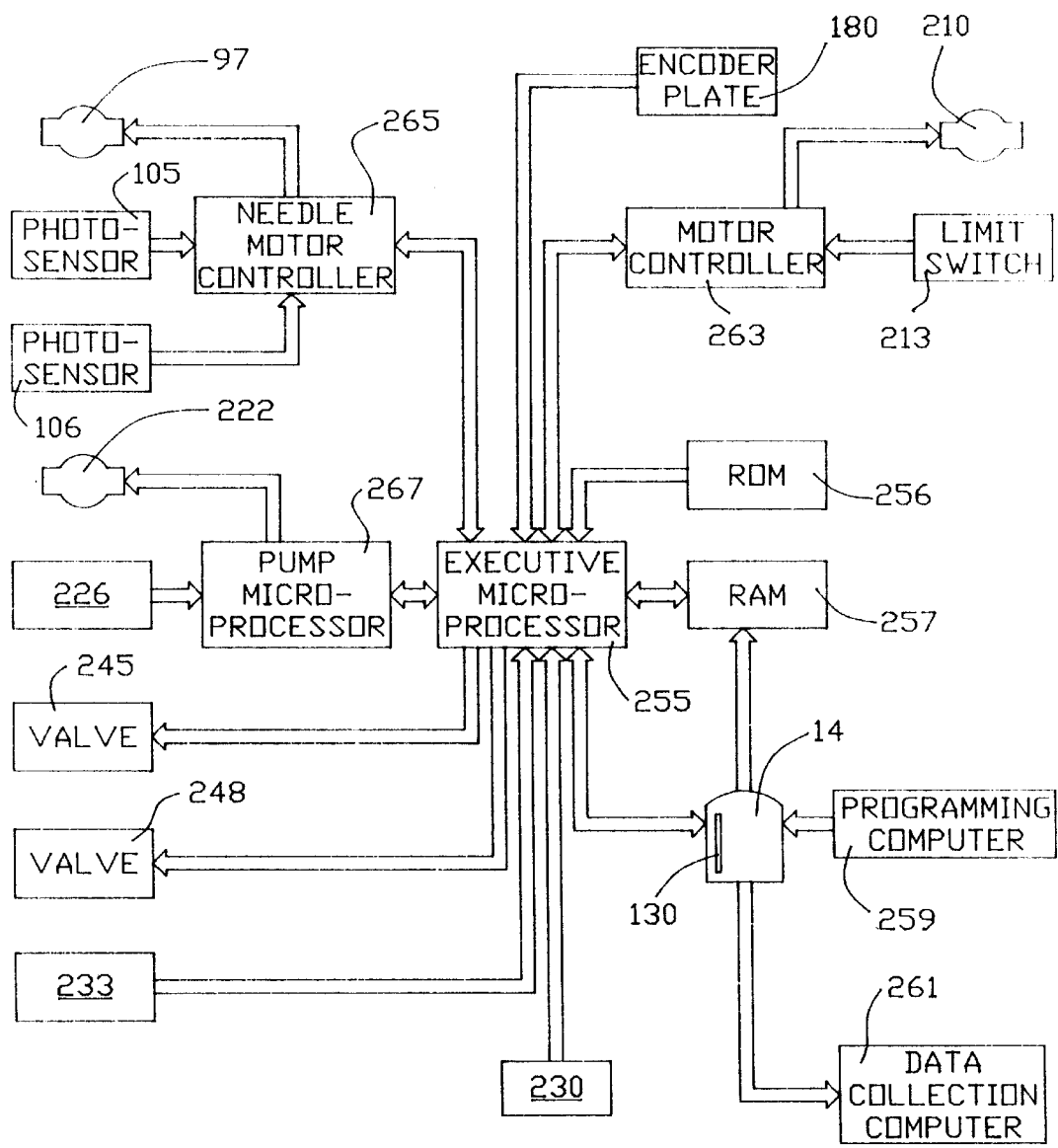
FIG. 13 is an expanded schematic diagram of the memory and control arrangement shown in FIG. 12.

Referring now to FIGS. 12 and 13, there is shown in schematic form the functions that are broadly incorporated within operations module 79. A gas stream, typically air, is drawn into the system through manifold 108 by operation of positive displacement pump 222. Pump 222 is turned on and off by signals 224 from executive microprocessor 255 in response to instructions 225 provided by electronic memory 130 that is contained in magazine 14. A mass flow controller 226 may be used to regulate the pumping rate, and also to inform memory 130 of the sample size or mass through signal connection 228.

In a preferred embodiment, measurements of various environmental properties of the ambient air that is being sampled are also monitored and the data obtained is transmitted to and stored in electronic memory 130. Monitored properties may include temperature, relative humidity, and the like. Sensors 233 and 235 may be provided to measure temperature and relative humidity. Data obtained from sensors 233 and 235 are transmitted to memory 130 through executive microprocessor 255 by way of signal connection means 236 and 238 respectively. The pressure of the sample stream is measured by means of transducer 230, and the values obtained are transmitted to microprocessor 255 through signal connection 231. Pressure data thus obtained serves as an operational check on the system. The sample taking procedure normally operates within defined pressure limits. If the pressure is outside those normal limits it indicates a leak, or a collapsed tube, or an incorrect sample tube, or some other anomaly.

FIG. 13 is an expanded schematic diagram showing details of the relationship among the various modules making up the sampling and analysis system of this invention. The heart of the control system is the executive microprocessor 255 that responds to operating instructions contained in read only memory (ROM) 256 and random access memory (RAM) 257. Microprocessor 255 is provided additional information from a number of other sources including the rotational position of the carousel from encoder plate 180, pressure data from transducer 230, and sample taking instructions from nonvolatile memory 130 that is contained in the magazine 14. As is illustrated in the Figure, data is input into memory 130 by means of a programming computer 259 which is located at a base laboratory. Other data, such as the ambient conditions present during sample taking and the like, is input into memory 130 from executive microprocessor 255. All of that data are then retrieved from memory 130 by means of a data collection computer 261, and are collated with the analytical results from each sample tube to form a single file. That prevents mix-up of the sample taking and analytical data.

In carrying out the sampling procedure, with reference to all of the Figures, a binary signal derived from encoder plate 180 informs executive microprocessor 255 of the rotational position of carousel 133 relative to sample ports 160 and 162 or to another designated home position. Microprocessor 255 then activates motor controller 263 which causes gear motor 210 to turn Geneva wheel 212 for one complete revolution at which time a signal is transmitted to controller 263 from limit switch 213 that stops motor 210. A first sample tube 240 is then aligned with outer sample port 160, and a second sample tube 242 is aligned with inner sample port 162. Needle motor controller 265 is then activated by microprocessor 255 causing the upper and lower needle blocks 85 and 90 to be driven toward one another until upper needle pair 82,83 and lower needle pair 87,88 penetrate through the septa that seal the end caps of sample tubes 240 and 242. Valve 245 is caused to move to its second position upon receiving a signal 246 from microprocessor 255, thus opening a flow path for the gas sample from manifold 108 through inlet conduit 110, sample tube 240, outlet conduit 114, and second two-position valve 248 to pump inlet line 250, which connects to valve 245.

Executive microprocessor 255 then signals pump microprocessor 267 to start pump 212 and thereby draw a gas volume that is set by instructions from memory 130 through sample tube 240. Valve 245 is then signalled to move back to the first of its positions, thus stopping flow of gas through tube 240. Either immediately thereafter or at some later preset time, second two-position valve 248 is signalled by microprocessor 255 to move from its first to its second positions. That isolates sample tube 240, and connects sample tube 242 to pump inlet line 250. Valve 245 is then signalled to move to its second position opening up a flow path from manifold 108 to pump 222 through sample tube 242. After a preset volume of sample is drawn through sample tube 242, valve 245 is signalled to move back to its first position thereby isolating tube 242 from the pump. Pump microprocessor 267 is then signaled by executive microprocessor 255 to cease operation. The upper and lower needle blocks are again activated, this time to drive the blocks away from each other and withdraw the needles from the sample tube ends. Microprocessor 255 then instructs carousel 133 to incrementally rotate so that another pair of sample tubes is aligned with the sample ports. That procedure is repeated until the desired number of samples has been taken, or until all of the sample tubes contained within the magazine have been used.

At that time, the used magazine is removed from port 70, and a new magazine is inserted. The electronic memory of that new magazine will contain sampling instructions that may be the same as those contained in the first magazine, or may be different. In the meantime, the first magazine with its used sample tubes is transported to a laboratory for analysis. Data relating to sample properties is uniquely associated with each sample tube in the electronic memory 130, and that data is retrieved by the analyzing laboratory as the sample tubes are processed.

It is sometimes useful to take duplicate samples, one for immediate analysis and the other as an archival sample. Sample trapping module 12 may be arranged for duplicate samples to be taken either simultaneously or sequentially. In the event that duplicate samples are taken simultaneously, operations module 79 is preferably provided with two pumps 222, and valve 248 is arranged to connect one sorbent tube to each pump during the sampling operation.

Figure 14:
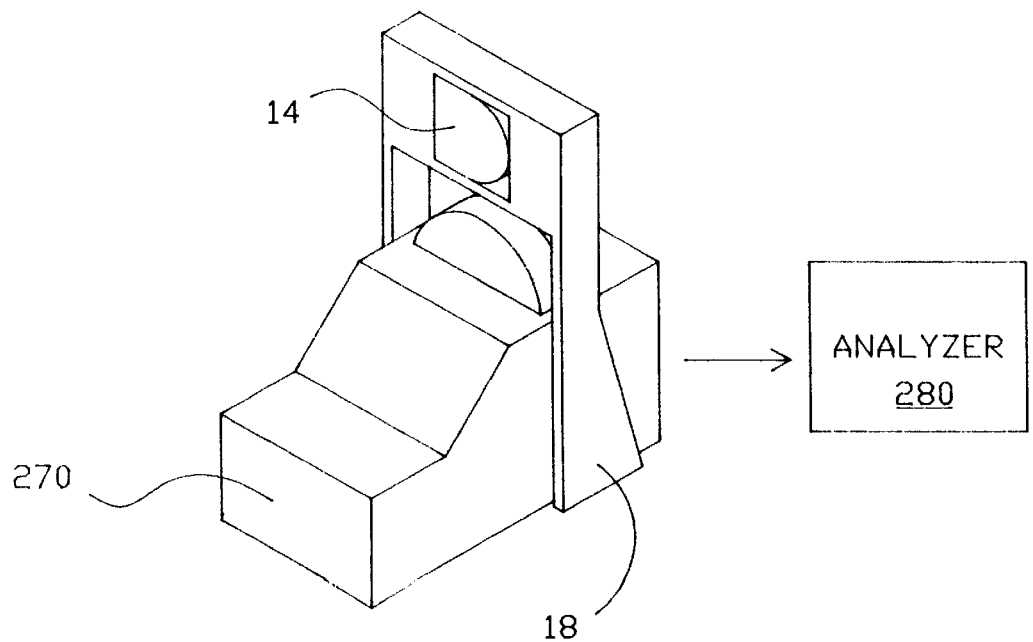
FIG. 14 is a schematic depiction of a system for the analysis of samples captured in the sample tubes of FIG. 2.

FIG. 14 is a diagram that illustrates a technique for the analysis of samples captured by the individual sample tubes. A magazine 14, having some or all of its contained sample tubes used for trapping samples, is transported to interface 18. Interface 18 functions to automatically remove sample tubes 16 from the magazine 14, one at a time, and load the sample tubes into a desorber 270. The identity of each sample tube and its associated data is maintained by tracking the position of the sample tube in the desorber device relative to its position in the carousel. Desorber 270 serves to quantitatively displace the collected contaminants from the collector material 33,34,35 contained within the sample tube. Displacement of the collected contaminants may be accomplished by means of a solvent extraction in the case of biological contaminants, or by thermal desorption in the case of chemical contaminants.

Automatic thermal desorbers for displacing collected contaminants from sample tubes similar in size and shape to those used in the inventive process are commercially available. One such desorber is sold by Perkin-Elmer Corporation, and is designated its model ATD 400. That particular device, or others similar to it, can readily be adapted for use in this system. Interface 18 cooperates with desorber 270 to remove sample tubes, in order and one at a time, from magazine 14 and then drop the tubes into the appropriate slot in the desorber carousel. An electronic bridge connects interface 18 to desorber 270 to correlate operations of the two devices and to keep track of and maintain the identity of the individual samples.

The contaminants that are collected in an individual sample tube are displaced from the collector material in desorber 270 by heating the sample tube, and sweeping it with a gas stream to carry the contaminants from the tube into an analytical device 280. Analytical device 280 is preferably a gas chromatograph, although any other conventional analytical techniques such as, for example, mass spectroscopy, liquid chromatography, capillary zone electrophoresis, infrared spectroscopy, and the like may find use. When using gas chromatography, a detector is selected that is appropriate to the kind and concentration of contaminants of interest. Examples of suitable detector systems include thermal conductivity detectors, flame ionization detectors, mass selective detectors, photoionization detectors, ultraviolet detectors, and other specialized detection systems.

It can be appreciated that the described invention provides a unique system to collect and to archive samples using solid state technology. Samples may be collected over a period of time that can range from minutes to hours per sample. That permits the characterization of the air or gas stream being sampled to determine virtually all contaminants that were present during the period in which sampling was conducted.

The embodiments of this invention in which exclusive rights are asserted are set out in the following claims.

We claim:
1. A gas sampling system comprising:
a plurality of sample tubes, each said tube containing a solid collector material, the ends of each said tube having a vacuum tight end closure, each said end closure having a pierceable septum;
a magazine arranged to store said plurality of sample tubes and having means to sequentially move individual sample tubes into and out of a sampling location; and
a sample trapping module having a port arranged to accept entry of said magazine, said port having means to make mechanical and electrical connection with said magazine when the magazine is seated in the port, said trapping module having a pair of hollow bore needles spaced apart on the same axis, the points of said needles facing each other, the needles arranged to move back and forth along said axis, and to penetrate through and withdraw from the end cap septa of a sample tube when said tube is at said sampling location.

2. The gas sampling system of claim 1 wherein the solid collector material contained in said sample tubes is selected to trap chemical contaminants that are contained in the gas being sampled.

3. The gas sampling system of claim 2 wherein said collector material is an adsorbent.

4. The gas sampling system of claim 1 wherein the solid collector material Contained in said sample tubes traps biological contaminants that are contained in the gas being sampled.

5. The gas sampling system of claim 4 wherein said collector material is a high efficiency filter.

6. The gas sampling system of claim 4 wherein said collector material is a culture medium.

7. The gas sampling system of claim 1 wherein said magazine includes non-volatile memory means arranged to transmit, to receive, and to store data, said stored data including instructions that direct and control said sample trapping module.

8. The gas sampling system of claim 7 wherein said instructions include the volume of the sample to be taken.

9. The gas sampling system of claim 7 wherein the data that is received and stored by said non-volatile memory comprises sampling data including temperature and pressure of the gas being sampled and total sample volume.

10. The gas sampling system of claim 1 wherein said magazine comprises a circular carousel that is incrementally rotatable around a central axis and is enclosed within a housing, said carousel having means to accept and hold a plurality of sample tubes arranged in a circle about its circumference.

11. The gas sampling system of claim 10 wherein said means to accept and hold a plurality of sample tubes comprises an upper and a lower sample tube holding plate, both said plates having a plurality of superimposed, equi-spaced, sample tube holding slots extending inwardly from the plate circumference toward the plate centers.

12. The gas sampling system of claim 11 wherein said tube holding slots are extended deeply enough for each slot to hold two sample tubes, wherein the two tubes in a slot are simultaneously presented at said sampling location, and wherein said trapping module includes a second pair of hollow bore needles disposed parallel to said first needle pair, the two needle pairs arranged to simultaneously penetrate the end cap septa of the two sample tubes within a single slot.

13. The gas sampling system of claim 11 wherein said slots are oriented at an acute angle to a radius of said sample tube holding plates so that the inner tube in each slot nests between two adjacent outer tubes.

14. The gas sampling system of claim 11 wherein each incremental rotation of said carousel is equal to the arc subtended between adjacent tube holding slots, and wherein said carousel includes a signal generating means that produces a different binary signal for each rotational position of said carousel.

15. The gas sampling system of claim 11 further including an interface means that is arranged to remove sample tubes from said carousel, one at a time, and load said tubes into a contaminant desorbing and analysis means.

16. The gas sampling system of claim 15 wherein said interface means maintains sample identity by tracking the position of each sample tube loaded into said desorbing and analysis means relative to the carousel position of that same sample tube.

* * * * *